United States Patent [19]

Shikhman et al.

[11] Patent Number: 5,429,636
[45] Date of Patent: Jul. 4, 1995

[54] CONDUCTIVE BODY TISSUE PENETRATING DEVICE

[75] Inventors: Oleg Shikhman, Bridgeport, Conn.;
Sydney D. Autry, Bellingham, Wash.

[73] Assignee: United States Surgical Corporation, Norwalk, Conn.

[21] Appl. No.: 133,590

[22] Filed: Oct. 8, 1993

[51] Int. Cl.⁶ .............................................. A61N 5/06
[52] U.S. Cl. ..................................... 606/41; 604/164; 604/264
[58] Field of Search .................. 606/41, 45, 46, 167, 606/172, 173, 185; 604/21, 51, 117, 264, 272, 274, 164, 165

[56] References Cited

U.S. PATENT DOCUMENTS

| | | | |
|---|---|---|---|
| 4,269,174 | 5/1981 | Adair | 606/49 |
| 4,269,192 | 5/1981 | Matsuo . | |
| 4,299,230 | 11/1981 | Kubota . | |
| 4,356,826 | 11/1982 | Kubota . | |
| 4,535,773 | 8/1985 | Yoon . | |
| 4,582,061 | 4/1986 | Fry . | |
| 4,869,717 | 9/1989 | Adair | 604/51 |
| 5,066,288 | 11/1991 | Deniega et al. . | |
| 5,083,573 | 1/1992 | Arms . | |
| 5,209,721 | 5/1993 | Wilk . | |
| 5,217,441 | 6/1993 | Shichman . | |
| 5,271,380 | 12/1993 | Riek et al. . | |

FOREIGN PATENT DOCUMENTS

| | | |
|---|---|---|
| 836392 | 8/1951 | Germany . |
| 1616107 | 4/1971 | Germany . |
| 537677 | 1/1977 | U.S.S.R. . |
| 9214514 | 9/1992 | WIPO . |

OTHER PUBLICATIONS

Derwin English Language Abstract of German Publication No. DT 2919-390 (11/80).

*Primary Examiner*—Peter A. Aschenbrenner
*Assistant Examiner*—Michael Peffley

[57] ABSTRACT

The present invention relates to an apparatus and method for penetrating body tissue. The apparatus comprises a handle member having an electrical connection port, a shaft member fabricated from an electrically conductive material and having a proximal end portion secured to the handle member so as to extend outwardly from the handle member. A housing fabricated from an electrically insulating material is concentrically positioned about the outwardly extending portion of the shaft member. The distal end portion of the shaft member is configured to extend outwardly from the housing sufficiently to facilitate penetration of the body tissue.

4 Claims, 3 Drawing Sheets

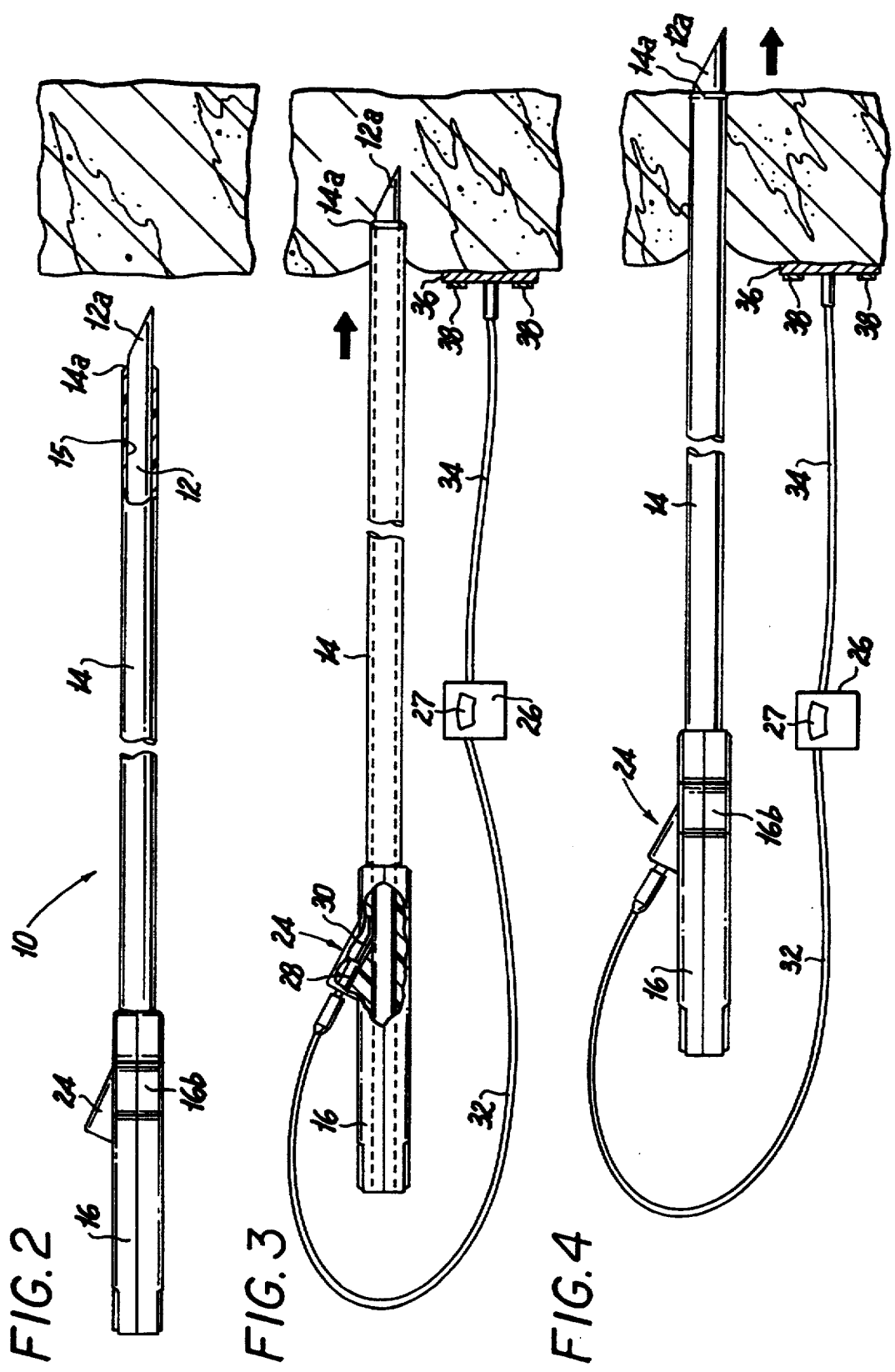

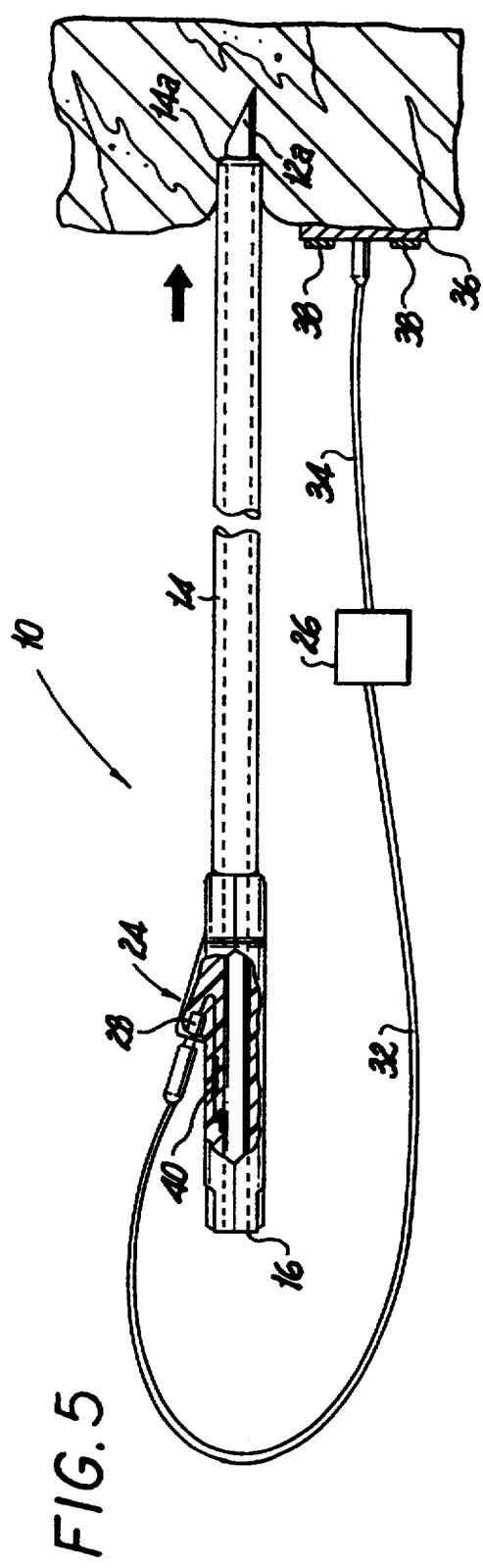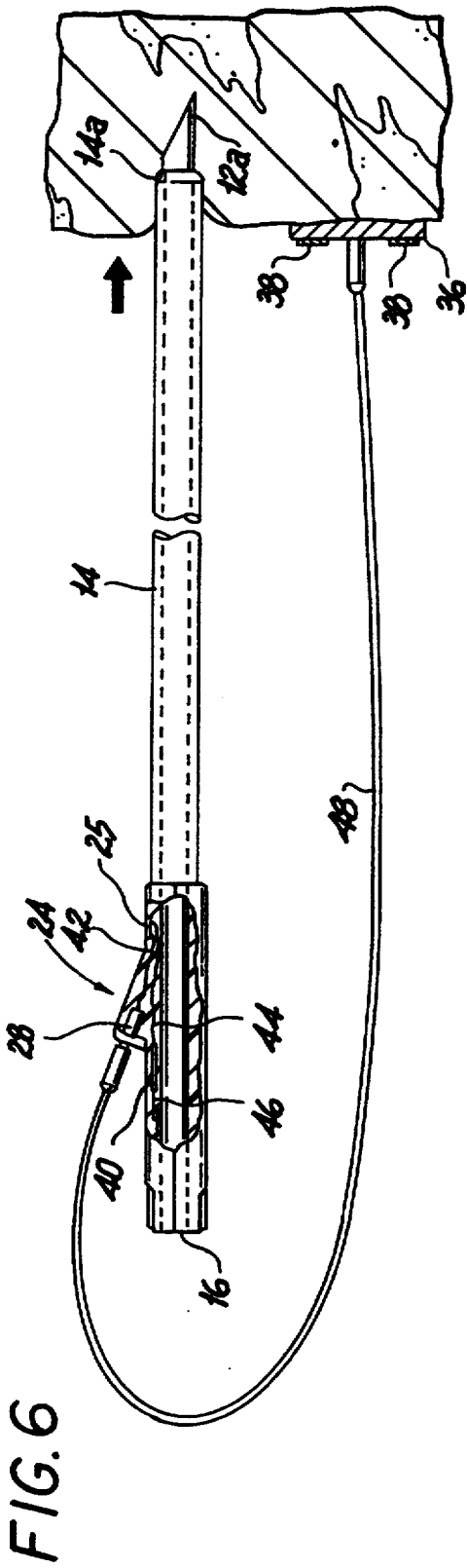

CONDUCTIVE BODY TISSUE PENETRATING DEVICE

BACKGROUND OF THE INVENTION

1. Field of the Invention

The present invention relates to an apparatus for penetrating body tissue. More particularly, the present invention relates to a pneumoperitoneum needle having an inner needle fabricated from an electrically conductive material and an outer sheath fabricated from an electrically insulating material.

2. Description of the Related Art

Pneumoperitoneum needles have been used to insufflate the abdominal cavity to facilitate laparoscopic and endoscopic examination and surgery of body tissue. One type of pneumoperitoneum needle, commonly known as the Veress-type pneumoneedle, includes a spring loaded blunt stylet in a larger diameter hollow needle. Once the pneumoneedle penetrates the abdominal wall and enters a body cavity, the resistance against the end of the needle ceases and the spring pushes the blunt end of the stylet forward so that it extends beyond the sharp tip of the needle. Thus when the needle penetrates the body tissue the sharp tip of the needle is prevented from puncturing or lacerating intra-abdominal structures.

Another Veress-type pneumoneedle is described in U.S. Pat. No. 5,139,485 to Smith et al. The needle described has a sharpened outer needle and allows passage of a blunt inner needle within the outer needle. In addition, the needle contains a position indicator within the outer needle which indicates whether the needle is in a protective or non-protective position. An acoustical enhancement mechanism is described which amplifies the sound of the inner needle moving to the protective position.

The present invention, on the other hand, provides a new and cost effective apparatus and method for detecting penetration of the peritoneum or other body portions by a hollow needle.

SUMMARY OF THE INVENTION

The present invention provides an apparatus for penetrating body tissue. In the preferred embodiment, the apparatus includes a shaft having a distal end portion adapted to conduct electricity and penetrate body tissue, and a proximal end portion configured and dimensioned for hand gripping. The proximal end portion of the shaft has an electric connection port secured thereto which is operatively connected to the distal end portion so as to facilitate an electrical connection between the distal end portion of the shaft and a remote measuring instrument. Generally, the current conducted through the shaft is a low-level current which prevents electrical cutting and/or cauterization of the body tissue.

In an alternative embodiment, the apparatus includes a handle member having an electrical connection port positioned thereon, a shaft fabricated from an electrically conductive material and a proximal end portion secured to the handle member and extending outwardly therefrom. The proximal end portion of the shaft includes at least a portion electrically connected to the electrical connection port, and housing means fabricated from an electrically insulating material concentrically positioned about the outwardly extending portion of the shaft such that a distal end portion of the shaft extends outwardly from the housing means.

In another alternative embodiment, the apparatus of the present invention includes a handle having a first longitudinal bore extending therethrough, an inner shaft member having a second longitudinal bore extending therethrough and a proximal end portion positioned at least partially within the first longitudinal bore. The inner shaft member has at least a portion thereof fabricated from an electrically conductive material, an outer housing concentrically positioned about the inner shaft member and a proximal end secured to a distal end of the handle. The outer housing is fabricated from an electrically insulating material and has a length less than the length of the inner shaft member. A distal end portion of the inner shaft member extends outwardly from the outer housing and electrical contact means positioned on the handle and is operatively connected to the electrically conductive portion of the inner shaft member.

A pneumoperitoneum needle is provided to facilitate insufflation of body cavities. The needle comprises a handle having a longitudinal bore therethrough, a hollow needle having a distal end portion adapted to penetrate body cavities and having a conduit for the passage of gases. The needle has a proximal end portion secured to the handle such that the longitudinal bore is in cooperative alignment with the conduit. An outer sheath is positioned about the needle and has a proximal portion secured to the handle. The outer sheath has a length less than the length of the needle such that a distal end portion of the needle extends outwardly from the sheath. Electric contact means is positioned on the handle and is operatively connected to the needle for transferring an applied electrical current from the exterior of the handle to the needle.

The invention also includes a method for penetrating body tissue. The method includes a step of providing an apparatus for penetrating body tissue. Preferably, the apparatus includes a shaft having a distal end portion adapted to conduct electricity and penetrate body tissue, and a proximal end portion configured and dimensioned for hand gripping. The proximal end portion of the shaft has an electric connection port secured thereto, which is operatively connected to the distal end portion so as to facilitate an electrical connection between the distal end portion of the shaft and a remote measuring instrument. The method also includes the steps of connecting an electrical measuring instrument between the shaft and the body tissue, positioning a distal end of the shaft against the body tissue, applying a low-level current to the shaft so that the current passes through the shaft to the body tissue when the distal end portion of the shaft contacts the body tissue and measuring the current with the measuring instrument. Pressure is then applied to the handle member so that the shaft is pressed against the body tissue so as to penetrate the body tissue, causing the measuring instrument to cease measuring the current.

BRIEF DESCRIPTION OF THE DRAWINGS

The preferred embodiments of the invention are described hereinbelow with reference to the drawings wherein:

FIG. 2 is a side elevational view of the needle assembly of FIG. 1 without the stopcock, illustrating the needle tip and sheath prior to insertion into the body tissue;

FIG. 3 is a side elevational view of the needle assembly of FIG. 1 without the stopcock, illustrating partial penetration of the needle assembly through the body tissue and the connections between an ohmmeter, the body tissue and the needle;

FIG. 4 is a side elevational view similar to FIG. 3, illustrating sufficient penetration of the conductive needle tip and insulating outer sheath to break the circuit between the body tissue and the needle, which is measured by an ohmmeter;

FIG. 5 is a side elevational view similar to FIG. 1, illustrating an internal energy source; and FIG. 6 is a side elevational view of an alternative embodiment for the needle assembly of the present invention, illustrating an internal energy source and indicator.

DETAILED DESCRIPTION OF THE PREFERRED EMBODIMENTS

Figure 1:
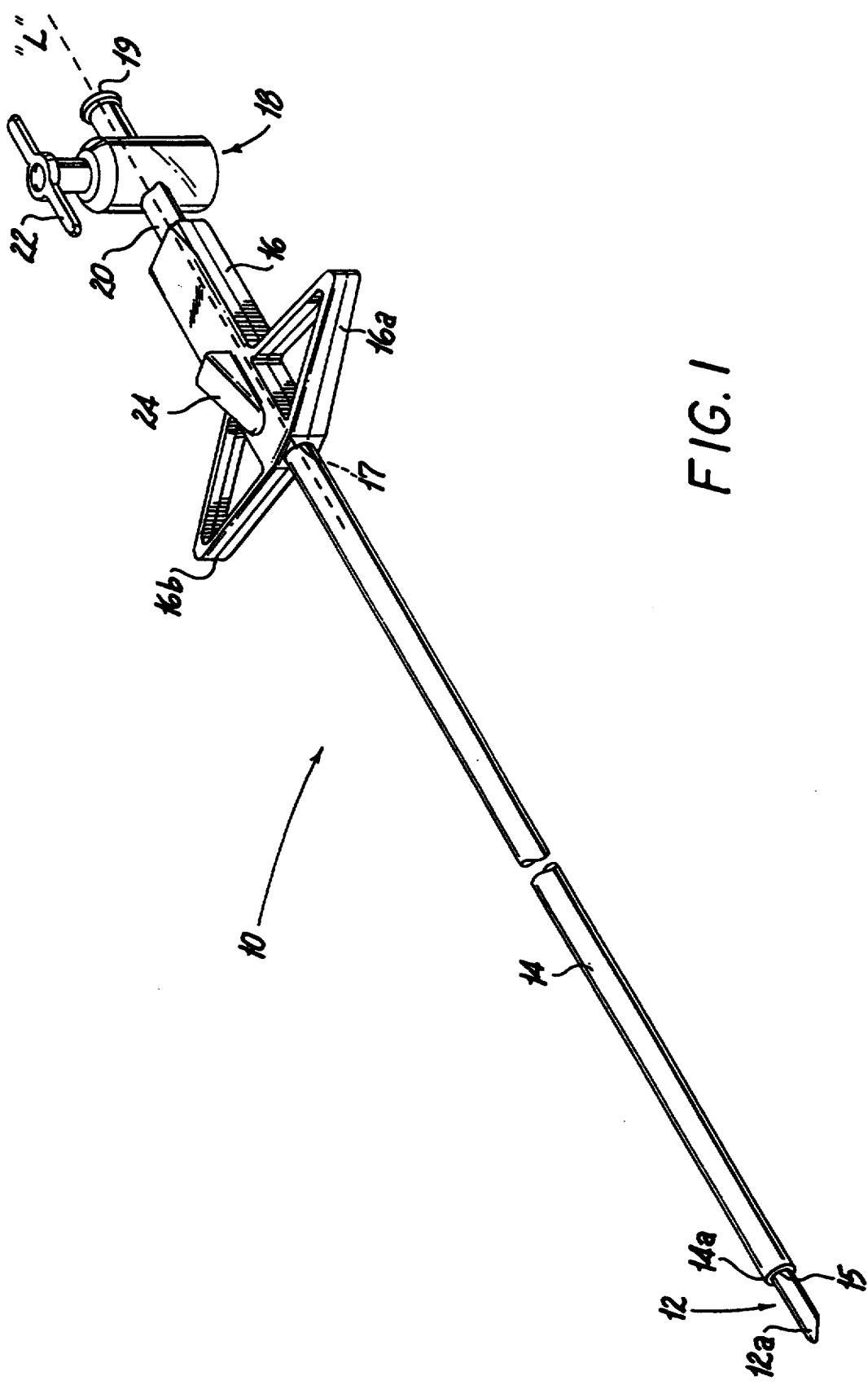
FIG. 1 is a perspective view of an exemplary needle assembly configured in accordance with the present invention and illustrating an insulating outer sheath and a conductive needle substantially within the outer sheath.

The apparatus of the present invention is provided to penetrate body tissue, e.g., the abdominal wall, and to provide an indication to the physician that the body tissue has been penetrated. In the preferred embodiment, the apparatus is a pneumoperitoneum needle 10 having handle 16, outer sheath 14 and electrically conductive inner needle 12. As shown in FIG. 1, the proximal end of outer sheath 14 is secured to the distal end of the handle.

Generally, handle 16 is configured to be held in several ways to allow for precision and control during insertion. Finger grips 16a and 16b are positioned at the distal end of handle 16 and extend substantially perpendicular to the longitudinal axis "L" of the handle. As noted above, outer sheath 14 is secured to the distal end of handle 16 such that the center channel 15 of sheath 14 is in coaxial alignment with a longitudinal bore 17 extending through handle 16 along longitudinal axis "L". Sheath 14 is fabricated from an electrically nonconductive material, i.e., an insulating material through which no electric current can flow. Preferably, sheath 14 is fabricated from polytetrafluorethylene (PTFE), otherwise known as TEFLON which is manufactured by DuPont.

Stopcock assembly 18 includes interface tube 20 and passageway 19 extending therethrough which are secured to the proximal end of handle 16 so that passageway 19 of interface tube 20 aligns with longitudinal bore 17 extending through handle 16. Stopcock 18 is provided to selectively allow insufflation and desufflation of the body cavity through the center channel of needle 12, once the needle has punctured the body tissue.

Inner needle 12 is a hollow tube fabricated from an electrically conductive material and includes a beveled distal end 12a to facilitate puncturing of the body tissue. Preferably, inner needle 12 is fabricated from stainless steel. Inner needle 12 is positioned within center channel 15 of outer sheath 14 and extends through the longitudinal bore 17 of handle 16 so that the hollow center of inner needle 12 is in alignment with passageway 19 of stopcock assembly 18. Thus, when valve lever 22 of stopcock 18 is rotated to an open position, insufflation gas is allowed to either enter or exit the body cavity.

The electrical connections for the needle assembly of the present invention will now be described with reference to FIGS. 2 and 3. Electrical connection port 24 is provided to facilitate an electrical connection between inner needle 12 and indicator 26. In the embodiment of FIGS. 3 and 4, indicator 26 is an ohmmeter which provides an external source of energy and an external indication of current flow. Whereas, in the embodiments of FIG. 5 and 6, indicator 26 is either an LED or like lighting member or a speaker, which upon completion of the circuit activates to provide a visual or audible indication, e.g., the LED lights, and upon penetration of the body tissue the indicator deactivates, e.g, the LED turns off.

Preferably, connection port 24 includes female receptacle 28 which receives a portion of a male electrical connector to provide a connection between the needle and the body tissue, and intermediate conductor 30 which is secured to receptacle 28 at one end and has the other end secured to inner needle 12, as shown in FIG. 3. Intermediate conductor 30 may be secured to inner needle 12 by solder, welds, conductive adhesives and the like. Alternatively, as shown in FIG. 5, needle 10 includes an internal source of energy, such as battery 40, which has one terminal connected to inner needle 12 and the other terminal connected to receptacle 28.

Conductor 32 provides the electrical connection between connection port 24 and indicator 26. Indicator 26 is also connected to the body tissue via conductor 34. Conductor 34 is secured to conductive plate 36 which is firmly secured to the body tissue by a suitable adhesive, such as surgical tape 38, so that an electrical connection is maintained between indicator 26 and the body tissue. In an alternative embodiment, conductive plate 36 may be an elongated plate positioned under a patient such that the weight of the patient maintains the electric connection between the plate and the body tissue.

An alternative embodiment of the electrical connections for the needle assembly of the present invention will be described with reference to FIG. 6. In this embodiment, the energy source and indicator are provided within handle 16 and electrical connection port 24 is provided to facilitate an electrical connection between the inner needle 12 and the body tissue. As shown, receptacle 28 of connector port 24 is connected to one terminal of indicator 25 via conductor 42. Another terminal of indicator 25 is connected to one terminal of the internal energy source, such as battery 40, via conductor 44. The other terminal of battery 40 connected to inner needle 12 via conductor 46, and conductor 48 provides the electrical connection between connection port 24 and the body tissue as shown. It should be noted that the connection to the body tissue for this embodiment is similar to the above described connections for the embodiment of FIG. 3.

In operation, the indicator is connected in the circuit between needle assembly 10 and the body tissue as shown in the Figures and described above. In the embodiment of FIG. 6, the indicator is positioned with the circuit so that a direct conductor 48 connects the needle to the body tissue. The surgeon then applies pressure to the proximal end of needle assembly 10, causing beveled end 12a of inner needle 12 to penetrate the body tissue, as shown in FIGS. 3 and 4. Engagement of the beveled end 12a of inner needle 12 with the body tissue completes the circuit between the needle assembly, the indicator and the body tissue so that a current flows from inner needle 12 through the body tissue and indicator 26 via conductors 32 and 34. For the embodiments of FIGS. 3 and 4, ohmmeter 26 then measures the resistance between inner needle 12 and the body tissue which can be visually observed from display 27 on ohmmeter 26. For the embodiments of FIGS. 5 and 6, the indicator activates, e.g., the LED lights, when the circuit is completed.

Preferably, the current flowing through inner needle 12 and the body tissue is in the microamp range so as to prevent cutting and/or cauterization of the body tissue. Typically the current is within the range of about 1 microampere and about 12 microamperes, preferably about 3 to about 10 microamperes. However, in instances where cutting and/or cauterization of the body tissue is necessary or desired, the current flowing through the body tissue may be increased to accomplish the desired cutting and/or cauterization effect. It should be noted that in instance where the current level is sufficient to cut body tissue, the distal end portion of the inner needle need not be beveled to facilitate penetration of the body tissue.

Once beveled end 12a of inner needle 12 completely penetrates the body tissue so that the distal end 14a of outer sheath 14 prohibits the needle from contacting the body tissue, as shown in FIG. 4, the circuit between the inner needle, the indicator and the body tissue is inhibited or broken. For the embodiments of FIGS. 3 and 4, ohmmeter 26 will see infinite or very high resistance between the inner needle and the body tissue, which can be visually observed from the ohmmeter display, thus indicating that the beveled end of the inner needle has entered the body cavity. Additionally, the ohmmeter 26 may provide an audible indication when the circuit resistance exceeds the appropriate value. For the embodiments of FIGS. 5 and 6, indicator 26 will deactivate, e.g., the LED will turn off, thus indicating that the beveled end of the inner needle has entered the body cavity.

It will be understood that various modifications can be made to the embodiments of the present invention herein disclosed without departing from the spirit and scope thereof. For example, various sizes of the instrument are contemplated, as well as various types of conductive and insulating materials. Also, various modifications may be made in the configuration of the parts. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. A method for penetrating body tissue comprising:
providing an apparatus for penetrating body tissue, said apparatus includes a shaft having a distal end portion adapted to conduct electricity and penetrate body tissue, and a proximal end portion having an electric connection port secured thereto and operatively connected to said distal end portion so as to facilitate an electrical connection between said distal end portion of said shaft, a circuit energizing source and indicator means, and means for interrupting said electrical connection upon penetration of body tissue;
coupling said indicator means to said electric connection port and to the body tissue;
applying a current to said shaft such that said current passes through said shaft, said indicator means and the body tissue when said distal end portion of said shaft contacts the body tissue; and
penetrating the body tissue with said apparatus for penetrating body tissue such that said indicating means indicates said current flow when penetrating the body tissue and ceases to indicate said current flow when the body tissue is penetrated.

2. The method according to claim 1, wherein said current is in the microamp range to prevent electrical cutting or cauterization of the body tissue.

3. The method according to claim 2, wherein said current ranges between about 1 microamp and about 12 microamps.

4. The method according to claim 3, wherein said current ranges between about 3 microamps to about 10 microamps.

* * * * *